United States Patent
Xiao et al.

(10) Patent No.: US 11,077,206 B2
(45) Date of Patent: Aug. 3, 2021

(54) COMPOSITION FOR GENE THERAPY OR TRANSFECTION, AND PREPARATION METHOD AND USE THEREOF

(71) Applicant: SHANGHAI CHANGZHENG HOSPITAL, Shanghai (CN)

(72) Inventors: Jianru Xiao, Shanghai (CN); Wanwan Shen, Shanghai (CN); Xiaopan Cai, Shanghai (CN); Yiyun Cheng, Shanghai (CN)

(73) Assignee: SHANGHAI CHANGZHENG HOSPITAL, Shanghai (CN)

(*) Notice: Subject to any disclaimer, the term of this patent is extended or adjusted under 35 U.S.C. 154(b) by 189 days.

(21) Appl. No.: 16/465,573

(22) PCT Filed: Sep. 6, 2018

(86) PCT No.: PCT/CN2018/104333
§ 371 (c)(1),
(2) Date: May 31, 2019

(87) PCT Pub. No.: WO2019/072055
PCT Pub. Date: Apr. 18, 2019

(65) Prior Publication Data
US 2019/0290779 A1     Sep. 26, 2019

(30) Foreign Application Priority Data
Oct. 9, 2017 (CN) ............................ 20170930826.1

(51) Int. Cl.
| | | |
|---|---|---|
| *A61K 48/00* | (2006.01) |
| *A61K 47/34* | (2017.01) |
| *C12N 15/113* | (2010.01) |
| *C12N 15/87* | (2006.01) |
| *A61K 47/22* | (2006.01) |
| *A61P 25/18* | (2006.01) |
| *A61K 47/30* | (2006.01) |
| *A61P 37/02* | (2006.01) |
| *A61K 31/353* | (2006.01) |
| *A61P 17/00* | (2006.01) |
| *A61P 29/00* | (2006.01) |
| *A61P 35/00* | (2006.01) |
| *A61P 5/00* | (2006.01) |
| *A61P 9/00* | (2006.01) |

(52) U.S. Cl.
CPC ........ *A61K 48/0041* (2013.01); *A61K 31/353* (2013.01); *A61K 47/22* (2013.01); *A61K 47/30* (2013.01); *A61K 47/34* (2013.01); *A61K 48/00* (2013.01); *A61P 5/00* (2018.01); *A61P 9/00* (2018.01); *A61P 17/00* (2018.01); *A61P 25/18* (2018.01); *A61P 29/00* (2018.01); *A61P 35/00* (2018.01); *A61P 37/02* (2018.01); *C12N 15/1137* (2013.01); *C12N 15/87* (2013.01)

(58) Field of Classification Search
None
See application file for complete search history.

(56) References Cited

U.S. PATENT DOCUMENTS

2016/0122757 A1* 5/2016 Nudler ................ C12N 15/113
514/44 A

FOREIGN PATENT DOCUMENTS

KR     101369716 B1 * 3/2014

OTHER PUBLICATIONS

Machine translation of KR-101369716, Mar. 2014, 16 pages.*

* cited by examiner

*Primary Examiner* — Tracy Vivlemore

(57) ABSTRACT

A composition for gene therapy or transfection includes nucleic acid, natural polyphenol, and cationic molecules. There are several phenolic hydroxyl groups in the natural polyphenol, so as to eliminate free radicals, prevent cancer, fight inflammation, and provide antioxidants feature. Compared with the delivery of cationic molecules alone, the composition can significantly improve the transfection efficiency by about 60-70%, reduce the dose of effective transfection of cationic molecules by about 20 times, thereby reducing the toxicity of transfection and showing better organism compatibility. The composition of the present invention does not introduce other chemical reagents, does not require synthesis, has high biosafety, and can efficiently and safely deliver a plurality of nucleic acid molecules into cells. The composition can be used as a highly effective and low-toxicity nucleic acid drug in the treatment of gene-related diseases, and has good medicinal value.

1 Claim, 10 Drawing Sheets

COMPOSITION FOR GENE THERAPY OR TRANSFECTION, AND PREPARATION METHOD AND USE THEREOF

CROSS REFERENCE OF RELATED APPLICATION

This is a U.S. National Stage under 35 U.S.C 371 of the International Application PCT/CN2018/104333, filed Sep. 6, 2018, which claims priority under 35 U.S.C. 119(a-d) to CN 201710930826.1, filed Oct. 9, 2017.

BACKGROUND OF THE PRESENT INVENTION

Field of Invention

The present invention relates to a composition for gene therapy or transfection, belonging to a technical field of biochemistry and biomaterials.

Description of Related Arts

Gene therapy as a new treatment is widely used to treat a variety of diseases, such as tumors, hereditary diseases, inflammation, immune disorders, endocrine disorders, mental disorders and cardiovascular diseases. It mainly achieves the therapeutic effect by introducing foreign genes into target cells to change the transcriptional translation of existing genes, the expression of proteins, and the synthesis of biological enzymes to regulate life activities. The success of gene therapy lies in the efficient and safe delivery of foreign genes into target cells. Therefore, efficient and safe gene vectors are the key.

Cationic molecules, as a large class of non-viral vectors, form a positively charged complex with nucleic acid molecules through electrostatic interactions and enter cells by endocytosis. However, the transfection efficiency of cationic molecules is malignant cross-linking with cytotoxicity. The more positive charges of cationic molecules are, the larger the molecular weight is, and the better the transfection efficiency will be, but the higher the cytotoxicity will be. The cationic molecules with lower molecular weight have better peptide or polymer biocompatibility, but because the surface has a small positive charge and weakly binds to the nucleic acid, the weak complex becomes unstable when being interfered by molecules such as proteins and phospholipids, thereby releasing the nucleic acid in advance and lowering the transfection efficiency. The malignant cross-linking of transfection efficiency with cytotoxicity limits the development of cationic molecules in biomedical and clinical gene therapy.

Many gene transfection methods are complicated in the prior art, wherein the material synthesis process is complicated, the composition is uncontrollable, the gene transfection effect is not good, and the toxicity is high.

SUMMARY OF THE PRESENT INVENTION

The present invention solves the problem that the cationic molecule weakly binds to the nucleic acid by introducing the element of natural polyphenol. Natural polyphenols bind to nucleic acids by hydrogen bonding to form negatively charged nanoparticles, which are then combined with cationic molecules to help the cationic molecules to stabilize the nucleic acids and form more uniform nanoparticles (see FIG. 1 and FIG. 2), thereby increasing the transfection efficiency of the cationic molecules. The amount of cationic molecules is reduce, while good biosafety is provided. Compared with the delivery of cationic molecules alone, the composition can significantly improve the transfection efficiency by about 60-70%, reduce the dose of effective transfection of cationic molecules by about 20 times, thereby reducing the toxicity of transfection and showing better organism compatibility. The composition of the present invention does not introduce other chemical reagents, does not require synthesis, has high biosafety, can efficiently and safely deliver a plurality of nucleic acid molecules into cells, and simultaneously removes active oxygen generated during transfection by means of natural polyphenols. By utilizing the anti-tumor, anti-inflammatory, anti-oxidation effects of natural polyphenols itself, the role of the composition in the treatment of diseases such as tumors and inflammation can be fully exerted.

Accordingly, in order to accomplish the above objects, the present invention provides:

a composition for gene therapy or transfection, comprising: nucleic acid, natural polyphenol, and cationic molecules.

Preferably, the nucleic acid comprises one of siRNA, miRNA, lncRNA, mRNA and modified RNA.

Preferably, the nucleic acid comprises one of siRNA, miRNA, oligonucleotide, peptide nucleic acid and modified siRNA.

Preferably, the nucleic acid is siRNA or modified siRNA.

Preferably, the natural polyphenol is selected from a group consisting of flavanols, anthocyanins, flavonoids, flavonols and phenolic plant extracts.

Preferably, the natural polyphenol is selected from a group consisting of epigallocatechin gallate, epicatechin, epigallocatechin (EGCG), epicatechin gallate, tannin (TA), 1,2,3,4,6-pentanoylglucose, 1,2,3,6-tetragalloylglucose, 1,3,6-trigalloylglucose, proanthocyanidins, anthocyanins, ellagic acid and caffeic acid.

Preferably, the cationic molecules are selected from a group consisting of cationic polymers, cationic natural small molecule compounds, cationic polypeptide and positively charged proteins.

Preferably, the cationic molecules are selected from a group consisting of polyamide-amine dendrimers, polypropylene imine dendrimers, polylysine cationic polymers, branched polyethyleneimine cationic polymers and linear polyethyleneimine cationic polymers.

Preferably, the cationic molecules are a compound of formula I, formula II, formula III, formula IV or formula V:

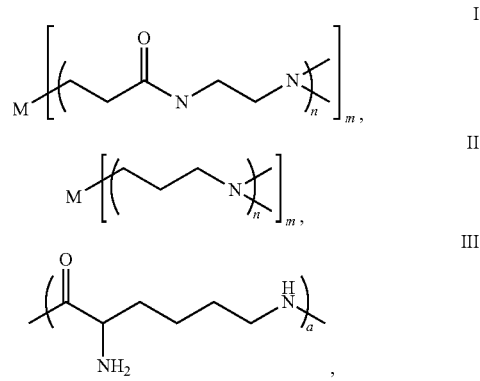

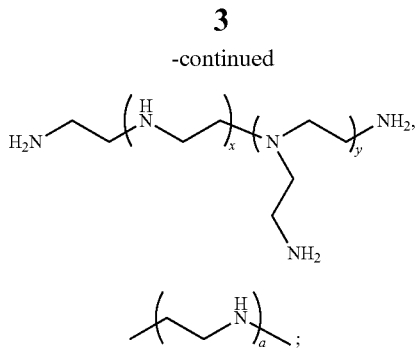

wherein M comprises one of ammonia, ethylenediamine, butanediamine, hexamethylenediamine, octanediamine, decanediamine and 1,12-dodecanediamine; n is an integer from 1 to 10, m is an integer from 2 to 4, and a is an integer from 1 to 100000; a mass average molecular weight of the compound of the formula III is from 100 to 100,000, a mass average molecular weight of the compound of the formula IV is from 100 to 100,000, and a mass average molecular weight of the compound of the formula V is from 100 to 100,000; the cationic polypeptide comprises cell penetrating peptide.

A preparation of the above composition is also provided, comprising a step of: mixing nucleic acid, natural polyphenol and cationic molecules in a predetermined mass ratio of 1:(0.01-100000):(0.01-100000).

A preparation method of a gene therapy or transfection medicine using the above composition is also provided.

Preferably, the gene therapy or transfection medicine is selected from a group consisting of oncology drugs, inflammatory drugs, immune disorder drugs, endocrine disorders drugs, psychosis drugs, cardiovascular and cerebrovascular drugs, and dermatological drugs.

Natural polyphenols are a class of polyphenolic compounds widely found in plants, including phenolic acids and flavonoids. There are several phenolic hydroxyl groups in the molecular structure of this polyphenolic compound, and many in vitro and in vivo experiments have proved that such polyphenolic compounds significantly eliminate free radicals, provide antioxidants feature, prevent UV rays, provide anti-obesity feature, prevent cardiovascular disease, fight inflammation, prevent and treat cancer. Therefore, such compounds are often used in supplements in health care products or cosmetics. At the same time, such molecules are also excellent hydrogen bond donors, capable of forming a complex with nucleic acids through hydrogen bonds and protecting nucleic acids from nuclease degradation.

Compared with the prior art, the present invention has the following beneficial effects:

The method described in the present invention does not introduce other chemical reagents, does not need to be synthesized, has natural materials, has high bio-safety, and can efficiently and greenly transport nucleic acids into cells, which can be used as an efficient, low-toxic, low-cost gene transfection method, so as to have a good application prospect in the treatment of gene-related diseases such as tumor, chronic enteritis, skin wound healing, immune disorder and the like.

BRIEF DESCRIPTION OF THE DRAWINGS

Other features, objects, and advantages of the present invention will become apparent from the following drawings and detailed description of non-limiting embodiments.

DETAILED DESCRIPTION OF THE PREFERRED EMBODIMENT

The present invention will now be described in detail in connection with embodiments. The following embodiments are intended to further illustrating but not limiting the present invention. It should be noted that a number of variations and modifications may be made by those skilled in the art without departing from the concept of the present invention. These are all within the scope of protection of the present invention.

Embodiment 1 relates to comparison of sizes and morphologies of siRNA/PLL and siRNA/EGCG/PLL complexes.

A complex was formed with natural polyphenol EGCG and luciferase siRNA (mass ratio 5:1) at a room temperature, then polylysine cationic polymer PLL was added, and the size and the morphology of the complex were observed by dynamic light scattering and transmission electron microscopy.

Figure 1:
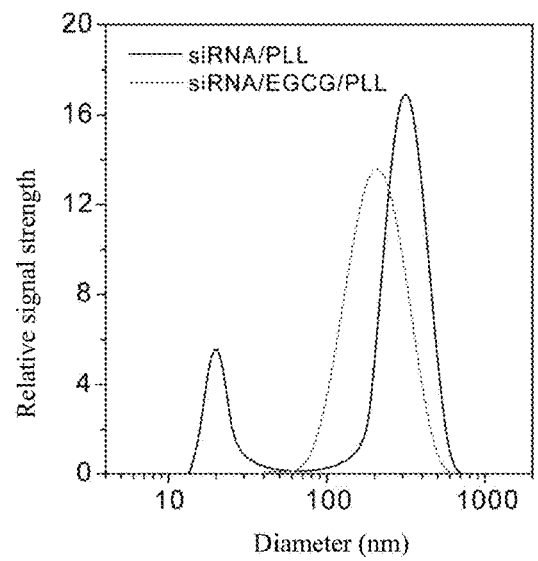
FIG. 1 illustrates sizes of two complexes of siRNA/PLL and siRNA/EGCG/PLL in an embodiment 1.

Experimental Results:

FIG. 1 illustrates the sizes of the siRNA/PLL and siRNA/EGCG/PLL complexes.

Figure 2:
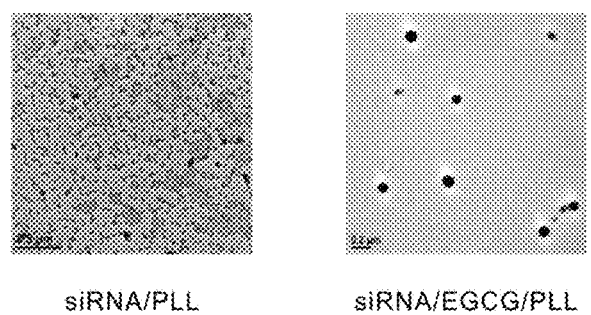
FIG. 2 illustrates morphologies of two complexes of siRNA/PLL and siRNA/EGCG/PLL in the embodiment 1.

FIG. 2 illustrates the electron microscopy morphologies of the SEM/PLL and siRNA/EGCG/PLL complexes. The results show that compared with PLL alone, the addition of EGCG allows the composite to form nanoparticles that are more uniform in size and better in morphology.

Embodiment 2 relates to cellular uptake of different complexes.

The natural polyphenol EGCG and the fluorescently labeled luciferase siRNA (FAM-siRNA) were combined at a room temperature, and then cationic polymer PLL and PAMAM were added (mass ratio siRNA:EGCG:PLL=1:5:5, siRNA:EGCG:PAMAM=1:10:10) before being added to the cells after incubation, so as to observe uptake of siRNA cells.

Figure 3:
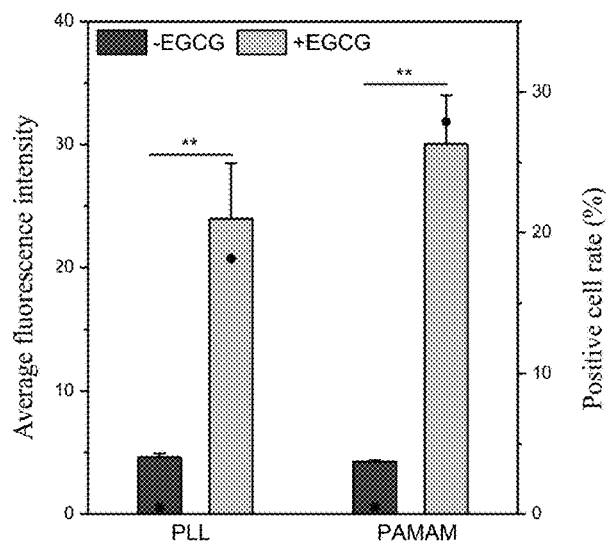
FIG. 3 illustrates endocytosis of different complexes in an embodiment 2.

Experimental Results:

FIG. 3 illustrates the cellular uptake of different complexes, which shows that compared to the cationic molecule alone, siRNA cells are enhanced by the addition of EGCG.

Embodiment 3 relates to the efficiency of knocking out luciferase genes in Hela-luci cells by different combinations of nucleic acid, natural polyphenol and cationic molecules.

The three components of the composition were incubated by different combinations at a room temperature before being transfected in HeLa-luci cells, and the gene transfection efficiency of the complex was evaluated by measuring the amount of luciferase expression.

Figure 4:
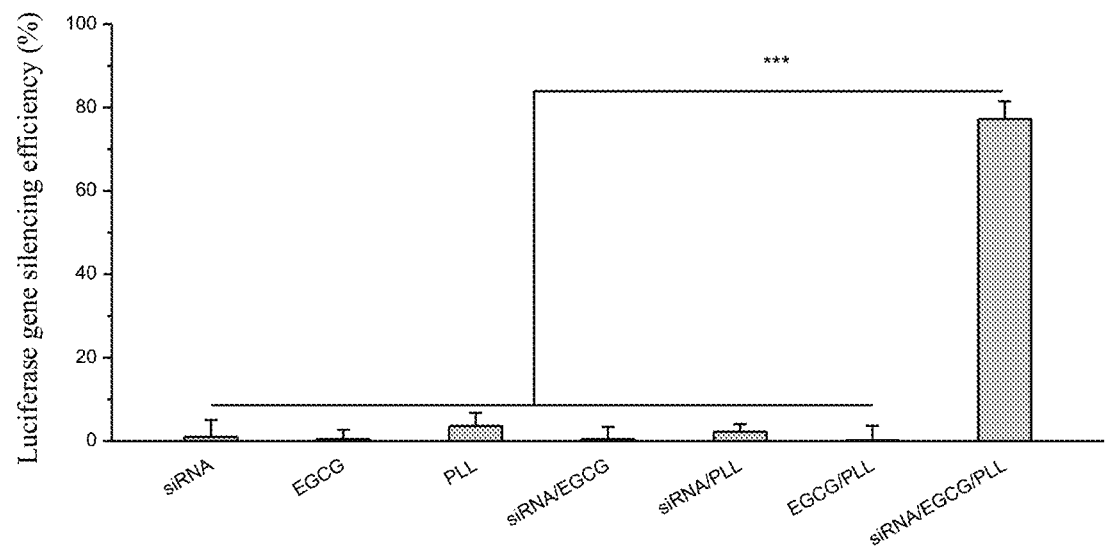
FIG. 4 illustrates efficiency of knocking out luciferase gene in Hela-luci cells by different combinations of three components of the composition (EGCG) in an embodiment 3.

Experimental Results:

FIG. 4 illustrates efficiency of knocking out luciferase gene in Hela-luci cells by different combinations of three components. The results show that if there is only one or two components, no matter how combined, the luciferase genes cannot be effectively knocked out. However, the three together (mass ratio siRNA:EGCG:PLL=1:5:5) can effectively knock out genes by up to 77.2%, which means these three components are indispensable.

Embodiment 4 relates the efficiency of knocking out luciferase genes in Hela-luci cells using different cationic polymers.

The natural polyphenol EGCG and luciferase siRNA (siLuc) were formed into a complex at a room temperature, and then different cationic molecules were added (mass ratio siRNA:EGCG:PLL=1:5:5, siRNA:EGCG:LPEI=1:5:5, siRNA:EGCG:DGL=1:10:10, siRNA:EGCG:BPEI=1:10:10, siRNA:EGCG:PPI=1:10:10, siRNA:EGCG:PAMAM=1:10:10), transfection was performed in Hela-luci cells after incubation, and the gene transfection efficiency of the complex was evaluated by measuring the amount of luciferase expression.

Figure 5:
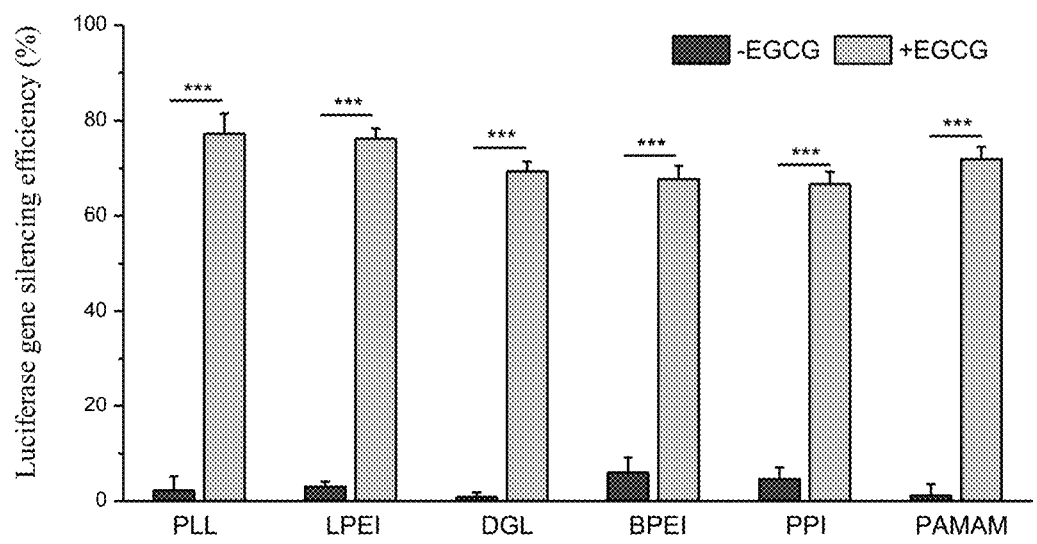
FIG. 5 illustrates efficiency of knocking out the luciferase gene in the Hela-luci cells using different cationic polymers of the composition (EGCG) in an embodiment 4.

Experimental Results:

FIG. 5 illustrates efficiency of knocking out the luciferase gene in the Hela-luci cells using different cationic polymers of the composition. The results show that all different cationic molecules can effectively knock out genes by 65-80%.

Embodiment 5 relates to specificity of knocking out the luciferase gene in the Hela-luci cells of the composition.

The natural polyphenol EGCG and luciferase siRNA (siLuc) and the nonsense siRNA (siNC) were formed into a complex at a room temperature, and then a polylysine cationic polymer PLL (mass ratio siRNA:EGCG:PLL=1:5:5, siNC:EGCG:PLL=1:5:5) was added, transfection was performed in HeLa-luci cells after incubation, and the gene transfection efficiency of the complex was evaluated by measuring the amount of luciferase expression.

Figure 6:
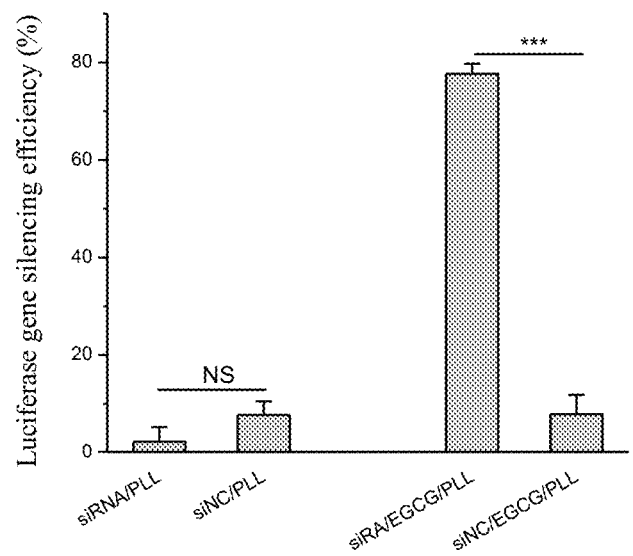
FIG. 6 illustrates specificity of knocking out the luciferase gene in the Hela-luci cells of the composition (EGCG) in an embodiment 5.

Experimental Results:

As shown in FIG. 6, only the siRNA group gene is effectively knocked out, and the siNC group has no effective gene silencing. The results show that the gene silencing effect of the composition has specificity, and no non-targeted knockout occurs.

Embodiment 6 relates to efficiency and specificity of knocking out the luciferase gene in human breast cancer cells (MDA-MB-231) by the composition.

The natural polyphenol EGCG and luciferase siRNA (siLuc) and the nonsense siRNA (siNC) were formed into a complex at a room temperature, and then a polylysine cationic polymer PLL (mass ratio siRNA:EGCG:PLL=1:20:20, siNC:EGCG:PLL=1:20:20) was added, transfection was performed in human breast cancer cells (MDA-MB-231) after incubation, and the gene transfection efficiency of the complex was evaluated by measuring the amount of luciferase expression.

Figure 7:
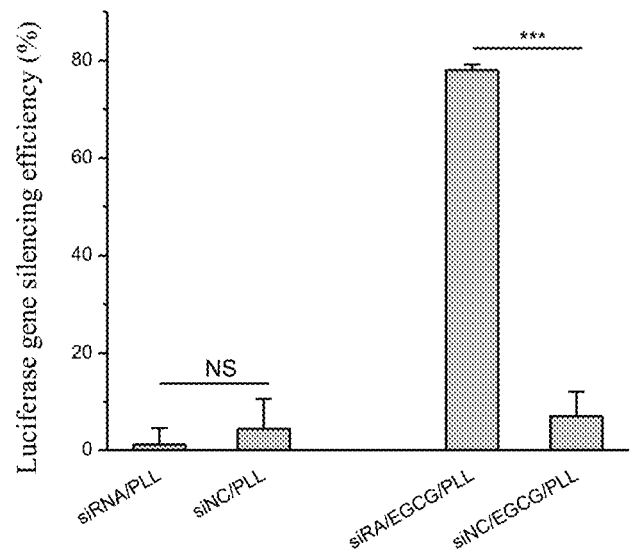
FIG. 7 illustrates efficiency and specificity of knocking out the luciferase gene in human breast cancer cells (MDA-MB-231) by the composition (EGCG) in an embodiment 6.

Experimental Results:

As shown in FIG. 7, this composition is also able to perform 78% gene silencing in human breast cancer cells (MDA-MB-231) without non-specific knockout.

Embodiment 7 relates to efficiency of knocking out matrix metalloproteinase MMP-9 in brain cancer cells U87 by the composition.

The natural polyphenol EGCG and MMP-9 siRNA and the non-significant sequence siRNA (siNC) were formed into a complex at a room temperature, and then a polylysine cationic polymer PLL (mass ratio siRNA:EGCG:PLL=1:5:5, siNC:EGCG:PLL=1:5:5) was added, transfection was carried out in U87 cells after incubation, and the gene transfection efficiency of the complex was evaluated by detecting the expression level of MMP-9 mRNA with fluorescent quantitative RT-PCR.

Figure 8:
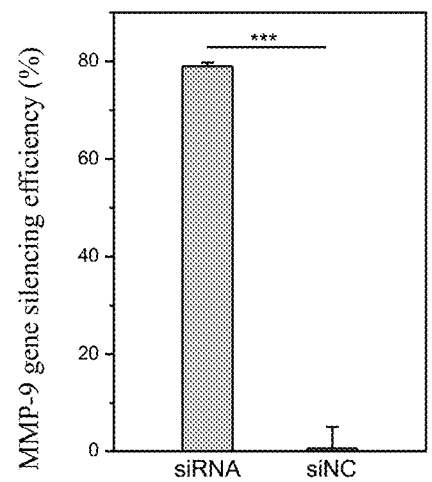
FIG. 8 illustrates efficiency of knocking out matrix metalloproteinase MMP-9 in brain cancer cells U87 by the composition (EGCG) in an embodiment 7.

Experimental Results:

As shown in FIG. 8, this composition is able to perform specific gene knockout in U87 cells with an efficiency of 79%.

Embodiment 8 relates to efficiency of knocking out glyceraldehyde-3-phosphate dehydrogenase GAPDH in human lung adenocarcinoma cells PC-9 by the composition.

The natural polyphenol EGCG and GAPDH siRNA and the nonsense siRNA (siNC) were formed into a complex at a room temperature, and then a polylysine cationic polymer PLL (mass ratio siRNA:EGCG:PLL=1:5:5, siNC:EGCG:PLL=1:5:5) was added, transfection was performed in PC-9 cells after incubation, and the gene transfection efficiency of the complex was evaluated by detecting the expression level of GAPDH mRNA with fluorescent quantitative RT-PCR.

Figure 9:
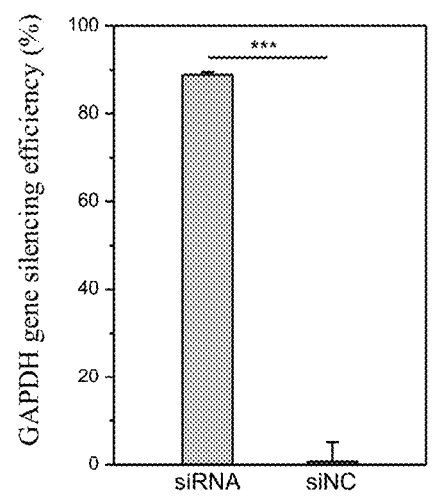
FIG. 9 illustrates efficiency of knocking out glyceraldehyde-3-phosphate dehydrogenase GAPDH in human lung adenocarcinoma cells PC-9 by the composition (EGCG) in an embodiment 8.

Experimental Results:

As shown in FIG. 9, this composition is able to perform specific gene knockout in PC-9 cells with an efficiency of 89%.

Embodiment 9 relates to efficiency of knocking out proline hydroxylase PHD2 in mouse fibroblast NIH-3T3 by the composition.

The natural polyphenol EGCG and PHD2 siRNA and the nonsense siRNA (siNC) were formed into a complex at a room temperature, and then a polylysine cationic polymer PLL (mass ratio siRNA:EGCG:PLL=1:5:5, siNC:EGCG:PLL=1:5:5) was added, transfection was performed in NIH-3T3 cells after incubation, and the gene transfection efficiency of the complex was evaluated by detecting the expression level of PHD2H mRNA with fluorescent quantitative RT-PCR.

Figure 10:
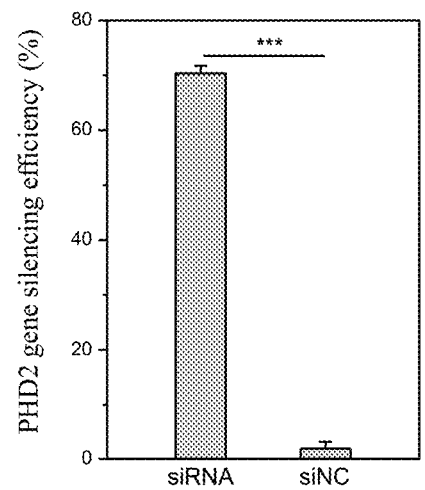
FIG. 10 illustrates efficiency of knocking out proline hydroxylase PHD2 in mouse fibroblast NIH-3T3 by the composition (EGCG) in an embodiment 9.

Experimental Results:

As shown in FIG. 10, this composition can perform specific gene knockout in NIH-3T3 cells with an efficiency of 70%.

Embodiment 10 relates to efficiency of knocking out the proline hydroxylase PHD2 in mouse intestinal epithelial cell IEC by the composition The natural polyphenol EGCG and PHD2 siRNA and the nonsense siRNA (siNC) were formed into a complex at a room temperature, and then a polylysine cationic polymer PLL (mass ratio siRNA:EGCG:PLL=1:5:5, siNC:EGCG:PLL=1:5:5) was added, transfection was performed in IEC cells after incubation, and the gene transfection efficiency of the complex was evaluated by detecting the expression level of PHD2H mRNA with fluorescent quantitative RT-PCR.

Figure 11:
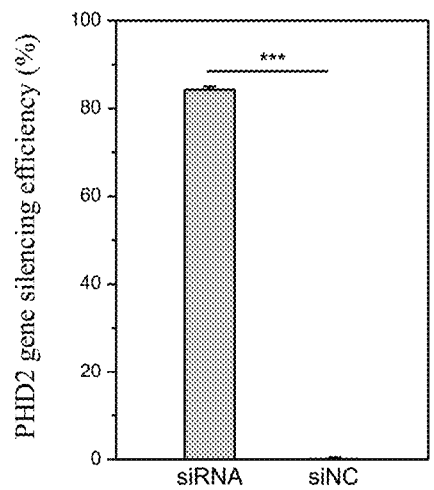
FIG. 11 illustrates efficiency of knocking out the proline hydroxylase PHD2 in mouse intestinal epithelial cell IEC by the composition (EGCG) in an embodiment 10.

Experimental Results:

As shown in FIG. 11, this composition can perform specific gene knockout in IEC cells with an efficiency of 84%.

Embodiment 11 relates to efficiency of knocking out the proline hydroxylase PHD2 in mouse macrophage RAW264.7 by the composition.

The natural polyphenol EGCG and PHD2 siRNA and the nonsense siRNA (siNC) were formed into a complex at a room temperature, and then a polylysine cationic polymer PLL (mass ratio siRNA:EGCG:PLL=1:5:5, siNC:EGCG:PLL=1:5:5) was added, transfection was performed RAW264.7 after incubation, and the gene transfection efficiency of the complex was evaluated by detecting the expression level of PHD2 mRNA with fluorescent quantitative RT-PCR.

Figure 12:
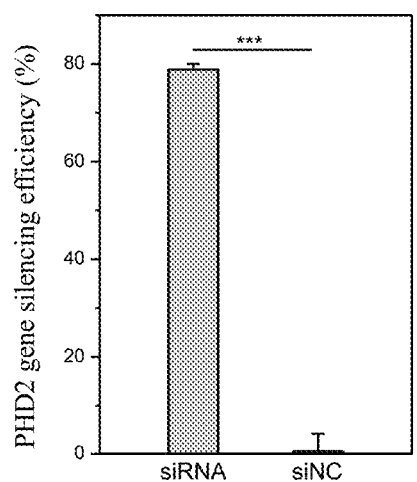
FIG. 12 illustrates efficiency of knocking out the proline hydroxylase PHD2 in mouse macrophage RAW264.7 by the composition (EGCG) in an embodiment 11.

Experimental Results:

As shown in FIG. 12, this composition is able to perform specific gene knockout in RAW264.7 cells with an efficiency of 79%.

Embodiment 12 relates treatment of chronic enteritis by knocking out proline hydroxylase PHD2 in mice with the composition.

BALB/c mouse enteritis was induced by dextran sulfate, and the composition (mass ratio siRNA:EGCG:PLL=1:5:5, siNC:EGCG:PLL=1:5:5) was administered from the anus. PHD2 siRNA was delivered to the intestine of mice to observe the development of mouse enteritis disease. After 8 days, the mice showed signs of inflammation (weight change, stool condition, intestinal bleeding) and scored. Tissue RNA was then extracted, and PHD2 and TNF-α mRNA levels were measured by RT-PCR to evaluate the therapeutic effect of this composition in mouse enteritis. Normal rats, phosphate buffer (PBS) and siNC were used as controls.

Figure 13:
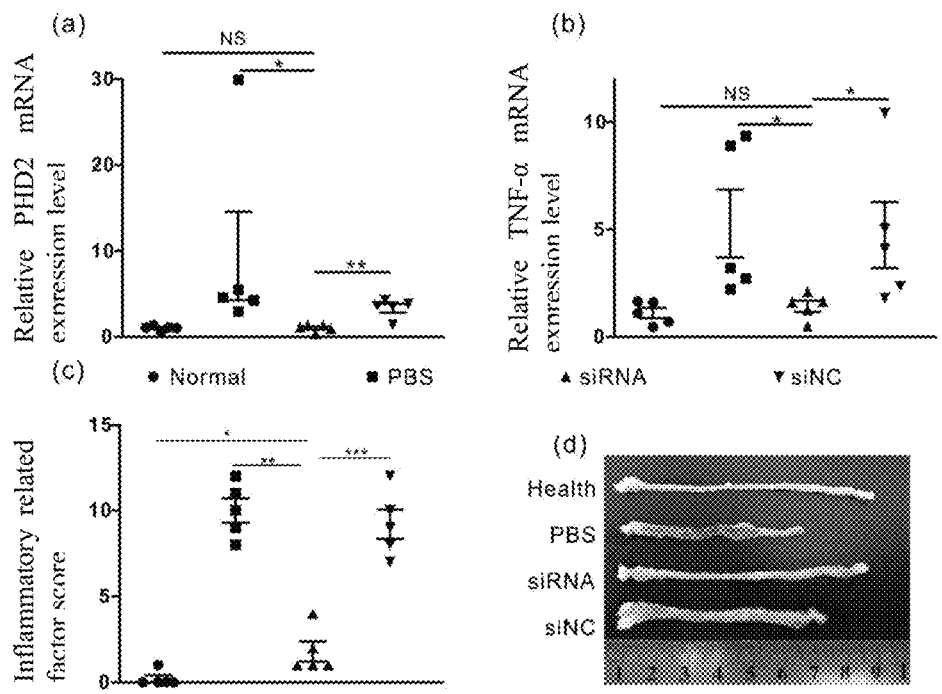
FIG. 13 illustrates effect of knocking out the proline hydroxylase PHD2 in mouse enteritis and a therapeutic effect thereof by the composition (EGCG) of an embodiment 12.

Experimental Results:

As shown in FIG. 13, in the mouse, the composition can also effectively knock out the PHD2 gene in the intestine of the mouse, and down-regulate the expression of the inflammation-related factor TNF-α, thereby inhibiting the development of inflammation. The experimental results show that the composition can regulate the expression of inflammation-related genes through gene silencing, thereby effectively controlling the progression of the disease.

Embodiment 13 relates to efficiency of knocking out the luciferase gene in the Hela-luci cells using different cationic polymers.

The natural polyphenol TA and luciferase luciferase siRNA (siLuc) were formed into a complex at a room temperature, and then different cationic molecules were added (mass ratio siRNA:TA:PLL=1:2:5, siRNA:TA:LPEI=1:2:5, siRNA:TA:PAMAM=1:1:10), transfection was performed in Hela-luci cells after incubation, and the gene transfection efficiency of the complex was evaluated by measuring the amount of luciferase expression.

Figure 14:
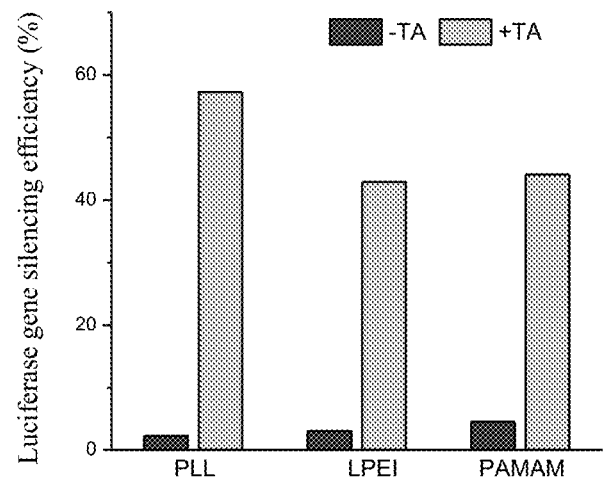
FIG. 14 illustrates efficiency of knocking out the luciferase gene in the Hela-luci cells using different cationic polymers of a composition (TA) in an embodiment 13.

Experimental Results:

FIG. 14 illustrates efficiency of knocking out the luciferase gene using different cationic polymers in the composition. The results show that all different cationic molecules are able to effectively knock out the gene by up to 40-55%.

Embodiment 14 relates to efficiency of knocking out the luciferase gene in the Hela-luci cells by a composition (catechin).

The natural polyphenol catechin and luciferase siRNA (siLuc) were formed into a complex at a room temperature, then different cationic molecules (mass ratio siRNA:catechin:LPEI=1:10:10) were added, transfection was performed in Hela-luci cells after incubation, and the gene transfection efficiency of the complex was evaluated by measuring the amount of luciferase expression.

Figure 15:
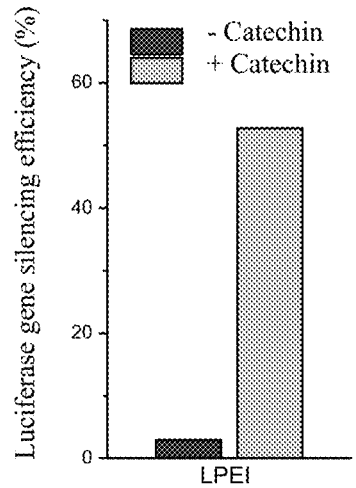
FIG. 15 illustrates efficiency of knocking out the luciferase gene in the Hela-luci cells by a composition (catechin) in an embodiment 14.

Experimental Results:

FIG. 15 illustrates efficiency of knocking out the luciferase gene by the composition. The results show that all different cationic molecules are able to effectively knock out genes by up to 52%.

Embodiment 15 relates to cytotoxicity of natural polyphenol EGCG in the Hela-luci cells A method for studying the cytotoxicity of the natural polyphenol EGCG in the present invention comprises steps of: incubating Hela-luci cells in a 96-well plate at a cell density of $10^4$ cells/well, removing a medium after incubation for 12 hours, and adding 100 μl fresh medium containing the siRNA whose concentration is the same as transfection concentration and a certain amount of EGCG, where the concentration of EGCG is from low to high (comprising the transfection concentration), and a final concentration is much higher than the transfection concentration; culturing for 24 hours, and measuring cytotoxicity by a MTT method.

Figure 16:
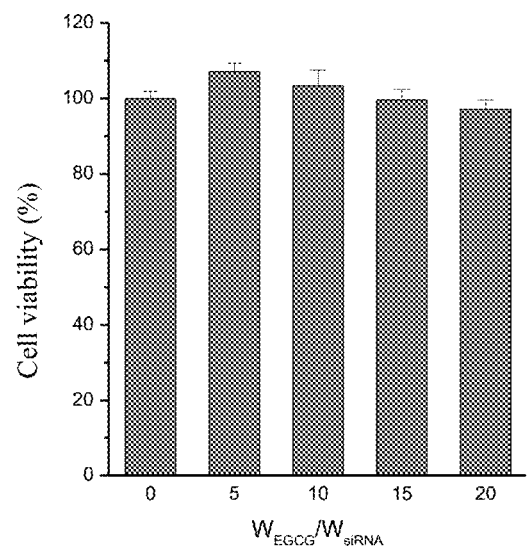
FIG. 16 illustrates cytotoxicity of EGCG in the HeLa-luci cells in an embodiment 15.

Experimental Results:

FIG. 16 illustrates cytotoxicity of natural polyphenol EGCG in the HeLa-luci cells. FIG. 16 shows that the natural polyphenol EGCG still has low cytotoxicity at a dose well above the transfection dose. A cell viability is more than 90%, showing low cytotoxicity.

Embodiment 16 relates to cytotoxicity of natural polyphenol EGCG and LPEI in the HeLa-luci cells.

A method for studying the cytotoxicity of the natural polyphenol EGCG and cationic polymer LPEI in the present invention comprises steps of: incubating Hela-luci cells in a 96-well plate at a cell density of $10^4$ cells/well, removing a medium after incubation for 12 hours, and adding 100 μl fresh medium containing the siRNA and LPEI whose concentration is the same as transfection concentration and a certain amount of EGCG, where the concentration of EGCG is from low to high (comprising the transfection concentration), and a final concentration is much higher than the transfection concentration; culturing for 24 hours, and measuring cytotoxicity by a MTT method.

Figure 17:
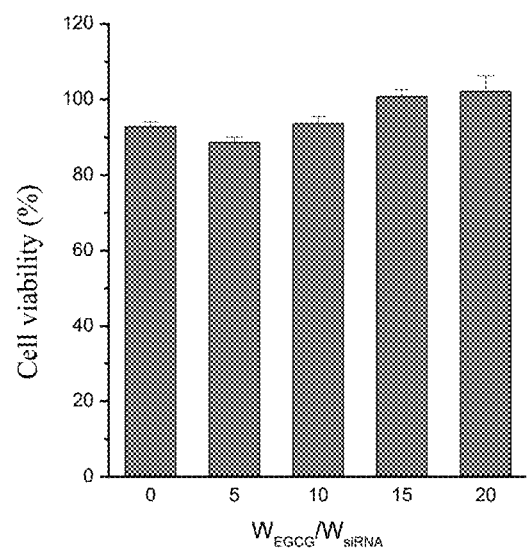
FIG. 17 illustrates cytotoxicity of EGCG and LPEI in the HeLa-luci cells in an embodiment 16.

Experimental Results:

FIG. 17 illustrates cytotoxicity of natural polyphenols EGCG and LPEI in the Hela-luci cells. FIG. 17 shows that in the presence of the cationic polymer, the natural polyphenol EGCG still has low cytotoxicity at a dose well above the transfection dose. A cell viability is more than 90%, showing low cytotoxicity.

Embodiment 17 relates to cytotoxicity of natural polyphenol EGCG and BPEI on Hela-luci cells A method for studying the cytotoxicity of the natural polyphenol EGCG and cationic polymer BPEI in the present invention comprises steps of: incubating Hela-luci cells in a 96-well plate at a cell density of $10^4$ cells/well, removing a medium after incubation for 12 hours, and adding 100 µl fresh medium containing the siRNA and BPEI whose concentration is the same as transfection concentration and a certain amount of EGCG, where the concentration of EGCG is from low to high (comprising the transfection concentration), and a final concentration is much higher than the transfection concentration; culturing for 24 hours, and measuring cytotoxicity by a MTT method.

Figure 18:
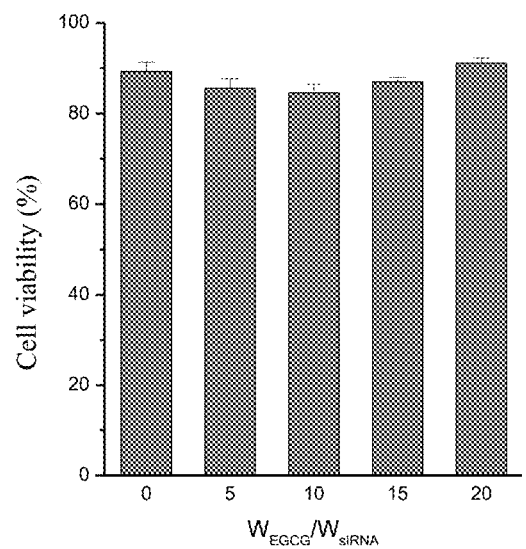
FIG. 18 illustrates cytotoxicity of EGCG and BPEI in the Hela-luci cells in an embodiment 17.

Experimental Results:

FIG. 18 illustrates cytotoxicity of natural polyphenols EGCG and BPEI in the Hela-luci cells. FIG. 18 shows that in the presence of the cationic polymer, the natural polyphenol EGCG still has low cytotoxicity at a dose well above the transfection dose. A cell viability is more than 90%, showing low cytotoxicity.

Embodiment 18 relates to cytotoxicity of natural polyphenol EGCG and PLL on Hela-luci cells A method for studying the cytotoxicity of the natural polyphenol EGCG and cationic polymer PLL in the present invention comprises steps of: incubating Hela-luci cells in a 96-well plate at a cell density of $10^4$ cells/well, removing a medium after incubation for 12 hours, and adding 100 µl fresh medium containing the siRNA and PLL whose concentration is the same as transfection concentration and a certain amount of EGCG, where the concentration of EGCG is from low to high (comprising the transfection concentration), and a final concentration is much higher than the transfection concentration; culturing for 24 hours, and measuring cytotoxicity by a MTT method.

Figure 19:
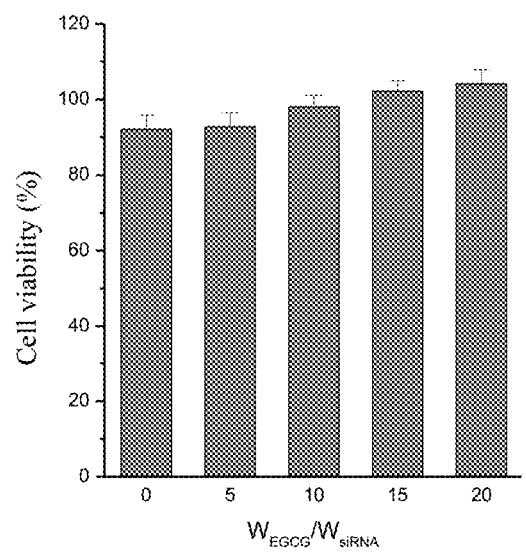
FIG. 19 illustrates cytotoxicity of EGCG and PLL in the HeLa-luci cells in an embodiment 18.

Experimental Results:

FIG. 19 illustrates cytotoxicity of natural polyphenols EGCG and PLL in the Hela-luci cells. FIG. 19 shows that in the presence of the cationic polymer, the natural polyphenol EGCG still has low cytotoxicity at a dose well above the transfection dose. A cell viability is more than 90%, showing low cytotoxicity.

Embodiment 19 relates to cytotoxicity of natural polyphenol EGCG and PAMAM G1 on Hela-luci Cells A method for studying the cytotoxicity of the natural polyphenol EGCG and cationic polymer PAMAM G1 in the present invention comprises steps of: incubating Hela-luci cells in a 96-well plate at a cell density of $10^4$ cells/well, removing a medium after incubation for 12 hours, and adding 100 µl fresh medium containing the siRNA and PAMAM G1 whose concentration is the same as transfection concentration and a certain amount of EGCG, where the concentration of EGCG is from low to high (comprising the transfection concentration), and a final concentration is much higher than the transfection concentration; culturing for 24 hours, and measuring cytotoxicity by a MTT method.

Figure 20:
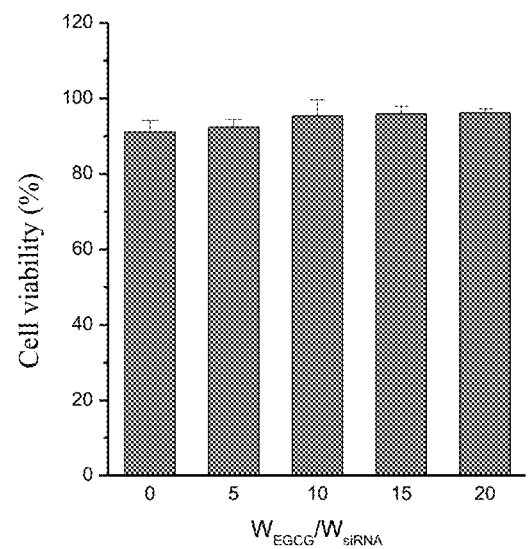
FIG. 20 illustrates cytotoxicity of EGCG and PAMAM G1 in the HeLa-luci cells in an embodiment 19.

Experimental Results:

FIG. 20 illustrates cytotoxicity of natural polyphenols EGCG and PAMAM G1 in the Hela-luci cells. FIG. 20 shows that in the presence of the cationic polymer, the natural polyphenol EGCG still has low cytotoxicity at a dose well above the transfection dose. A cell viability is more than 90%, showing low cytotoxicity.

Embodiment 20 relates to cytotoxicity of natural polyphenol EGCG and PAMAM G2 on Hela-luci cells A method for studying the cytotoxicity of the natural polyphenol EGCG and cationic polymer PAMAM G2 in the present invention comprises steps of: incubating Hela-luci cells in a 96-well plate at a cell density of $10^4$ cells/well, removing a medium after incubation for 12 hours, and adding 100 µl fresh medium containing the siRNA and PAMAM G2 whose concentration is the same as transfection concentration and a certain amount of EGCG, where the concentration of EGCG is from low to high (comprising the transfection concentration), and a final concentration is much higher than the transfection concentration; culturing for 24 hours, and measuring cytotoxicity by a MTT method.

Figure 21:
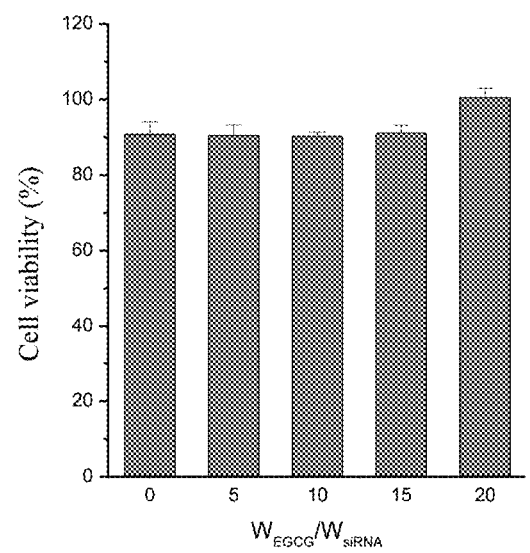
FIG. 21 illustrates cytotoxicity of EGCG and PAMAM G2 in the HeLa-luci cells in an embodiment 20.

Experimental Results:

FIG. 21 illustrates cytotoxicity of natural polyphenols EGCG and PAMAM G2 in the Hela-luci cells. FIG. 21 shows that in the presence of the cationic polymer, the natural polyphenol EGCG still has low cytotoxicity at a dose well above the transfection dose. A cell viability is more than 90%, showing low cytotoxicity.

The embodiments of the present invention have been described above. It is to be understood that the present invention is not limited to the embodiments described above, and various modifications and changes may be made by those skilled in the art without departing from the scope of the present invention.

What is claimed is:

1. A composition for gene therapy or transfection, comprising: siRNA or modified siRNA, epigallocatechin gallate, and polylysine cationic polymers.

* * * * *